United States Patent
Padrick et al.

(10) Patent No.: US 11,666,383 B2
(45) Date of Patent: Jun. 6, 2023

(54) SYSTEMS AND METHODS FOR INTRAOCULAR LENS SELECTION

(71) Applicant: Novartis AG, Basel (CH)

(72) Inventors: Thomas Padrick, Seattle, WA (US); Edwin J. Sarver, Cookeville, TN (US)

(73) Assignee: Alcon Inc., Fribourg (CH)

( * ) Notice: Subject to any disclaimer, the term of this patent is extended or adjusted under 35 U.S.C. 154(b) by 1077 days.

(21) Appl. No.: 16/239,771

(22) Filed: Jan. 4, 2019

(65) Prior Publication Data

US 2019/0209242 A1 Jul. 11, 2019

Related U.S. Application Data

(60) Provisional application No. 62/613,927, filed on Jan. 5, 2018.

(51) Int. Cl.
*A61B 34/10* (2016.01)
*A61B 3/00* (2006.01)
(Continued)

(52) U.S. Cl.
CPC ............ *A61B 34/10* (2016.02); *A61B 3/0025* (2013.01); *A61B 3/10* (2013.01); *A61F 2/16* (2013.01);
(Continued)

(58) Field of Classification Search
CPC ........ G16H 10/00–80/00; G06N 3/00–99/007; A61B 1/00–2576/026;
(Continued)

(56) References Cited

U.S. PATENT DOCUMENTS

| 6,626,538 B1 | 9/2003 | Arrowsmith |
| 7,044,604 B1 | 5/2006 | Arrowsmith |

(Continued)

FOREIGN PATENT DOCUMENTS

| CN | 103533882 A | * | 1/2014 | ........... A61B 3/0025 |
| EP | 1123689 A2 | | 8/2001 | |

(Continued)

OTHER PUBLICATIONS

Wang et al., "Comparison of Newer Intraocular Lens Power Calculation Methods for Eyes after Corneal Refractive Surgery," Ophthalmology . Dec. 2015;122(12):2443-9. doi: 10.1016/j.ophtha.2015.08.037. Epub Oct. 14, 2015. (Year: 2015).*

(Continued)

*Primary Examiner* — Jonathon A. Szumny
(74) *Attorney, Agent, or Firm* — Patterson + Sheridan, LLP

(57) ABSTRACT

Systems and methods for intraocular lens selection include obtaining one or more pre-operative measurements of an eye; selecting, from a plurality of historical IOL implantation records, a subset of historical IOL implantation records for evaluating a first plurality of prediction model candidates; evaluating the first plurality of prediction model candidates; selecting a first prediction model from the first plurality of prediction model candidates based on the evaluating; calculating, using the selected first prediction model, a plurality of estimated post-operative MRSE values based on a set of IOL powers and the one or more pre-operative measurements of the eye; determining a first IOL power corresponding to a first estimated post-operative MRSE value that matches a predetermined post-operative MRSE value; and providing the determined first IOL power to a user to aid in selection of an IOL for implantation in the eye.

20 Claims, 6 Drawing Sheets

(51) Int. Cl.
*G06F 30/20* (2020.01)
*G06N 20/00* (2019.01)
*G06N 20/20* (2019.01)
*G16H 20/40* (2018.01)
*G16H 50/20* (2018.01)
*A61B 3/10* (2006.01)
*A61F 2/16* (2006.01)

(52) U.S. Cl.
CPC ............ *G06F 30/20* (2020.01); *G06N 20/00* (2019.01); *G06N 20/20* (2019.01); *G16H 20/40* (2018.01); *G16H 50/20* (2018.01); *A61B 2034/108* (2016.02); *A61F 2240/002* (2013.01)

(58) Field of Classification Search
CPC .......................... G06F 1/00–2221/2153; A61F 2/00–2310/00994
See application file for complete search history.

(56) References Cited

U.S. PATENT DOCUMENTS

| | | |
|---|---|---|
| 8,657,445 B2 | 2/2014 | Olsen |
| 2005/0177313 A1* | 8/2005 | Latkany ................ A61F 2/1624 702/19 |
| 2009/0281552 A1 | 11/2009 | Hiramatsu et al. |
| 2016/0227996 A1* | 8/2016 | Neal ....................... A61B 3/107 |

FOREIGN PATENT DOCUMENTS

| | | | |
|---|---|---|---|
| JP | 2002119470 A | 4/2002 | |
| WO | WO-2012163980 A1 * | 12/2012 | ........... A61B 3/0025 |
| WO | WO-2017180914 A1 * | 10/2017 | ........... A61B 3/0025 |
| WO | WO2017180914 A1 | 10/2017 | |

OTHER PUBLICATIONS

Covert et al., "Intraocular Lens Power Selection in the Second Eye of Patients Undergoing Bilateral, Sequential Cataract Extraction," Ophthalmology . Jan. 2010;117(1):49-54. doi: 10.1016/j.ophtha.2009.06.020. Epub Oct. 7, 2009. (Year: 2010).*

Abulafia et al., "Prediction of refractive outcomes with toric intraocular lens implantation," J Cataract Refract Surg 2015; 41:936-944 ; http://dx.doi.org/10.1016/j.jcrs.2014.08.036. (Year: 2015).*

* cited by examiner

SYSTEMS AND METHODS FOR INTRAOCULAR LENS SELECTION

CROSS REFERENCE TO RELATED APPLICATION

This application claims priority to and the benefit of U.S. Provisional Patent Application No. 62/613,927 filed Jan. 5, 2018 and entitled "SYSTEMS AND METHODS FOR VECTOR IOL POWER CALCULATION," which is hereby incorporated by reference in its entirety.

BACKGROUND

Field of the Disclosure

The present disclosure relates to systems and methods to aid in the selection of an intraocular lens to be implanted.

Description of Related Art

Cataract surgery involves removing the natural lens of an eye and, in most cases, replacing the natural lens with an artificial intraocular lens (IOL). To achieve an optimal post-operative visual outcome, a good pre-operative surgical plan is crucial. Some of the important pre-operative planning decisions are the selection of an appropriate IOL type and power to achieve a desired manifest refraction in spherical equivalent (MRSE) after IOL implantation.

Typically, one or more prediction models may be used to determine an appropriate IOL type and power for a patient to achieve the desired MRSE based on, for example, pre-operative eye measurements of the patient. However, no prediction model can produce accurate results under all circumstances. For example, a first prediction model may produce more accurate results than a second prediction model under one set of circumstances, while the second prediction model may produce more accurate results than the first prediction model under a different set of circumstances. Thus, by using a fixed prediction model to determine appropriate IOL types and powers in all circumstances, the vision outcome of at least some of the patients may be suboptimal.

Therefore, there is a need in the art for techniques for better selecting an intraocular lens for implantation that leads to optimized vision outcomes for patients.

SUMMARY

According to some embodiments, a method includes obtaining, by one or more computing devices implementing a prediction engine, one or more pre-operative measurements of an eye for performing an intraocular lens (IOL) implantation in the eye; selecting, by the prediction engine from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power; evaluating, by the prediction engine, the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records; selecting, by the prediction engine, a first prediction model from the first plurality of prediction model candidates based on the evaluating; calculating, by the prediction engine using the selected first prediction model, a plurality of estimated post-operative MRSE values based on a set of available IOL powers and the one or more pre-operative measurements of the eye; determining, by the prediction engine from the set of available IOL powers, a first IOL power corresponding to a first estimated post-operative MRSE value from the plurality of estimated post-operative MRSE values that matches a predetermined post-operative MRSE value; and providing, by the prediction engine, the determined first IOL power to a user to aid in selection of an IOL for implantation in the eye.

According to some embodiments, a prediction engine includes one or more processors. The prediction engine is configured to obtain one or more pre-operative measurements of an eye for performing an intraocular lens (IOL) implantation in the eye; select, from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power; evaluate the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records; select a first prediction model from the first plurality of prediction model candidates based on the evaluating; calculate, using the selected first prediction model, a plurality of estimated post-operative MRSE values based on a set of available IOL powers and the one or more pre-operative measurements of the eye; determine, from the set of available IOL powers, a first IOL power corresponding to a first estimated post-operative MRSE value from the plurality of estimated post-operative MRSE values that matches a predetermined post-operative MRSE value; and provide, by the prediction engine, the determined first IOL power to a user to aid in selection of an IOL for implantation in the eye.

According to some embodiments, a non-transitory machine-readable medium comprising a plurality of machine-readable instructions which when executed by one or more processors are adapted to cause the one or more processors to perform a method. The method includes obtaining one or more pre-operative measurements of an eye for performing an intraocular lens (IOL) implantation in the eye; selecting, from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power; evaluating the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records; selecting a first prediction model from the first plurality of prediction model candidates based on the evaluating; calculating, using the selected first prediction model, a plurality of estimated post-operative MRSE values based on a set of available IOL powers and the one or more pre-operative measurements of the eye; determining, from the set of available IOL powers, a first IOL power corresponding to a first estimated post-operative MRSE value from the plurality of estimated post-operative MRSE values that matches a predetermined post-operative MRSE value; and providing the determined first IOL power to a user to aid in selection of an IOL for implantation in the eye.

BRIEF DESCRIPTION OF THE DRAWINGS

For a more complete understanding of the present technology, its features, and its advantages, reference is made to the following description, taken in conjunction with the accompanying drawings.

Figure 1:
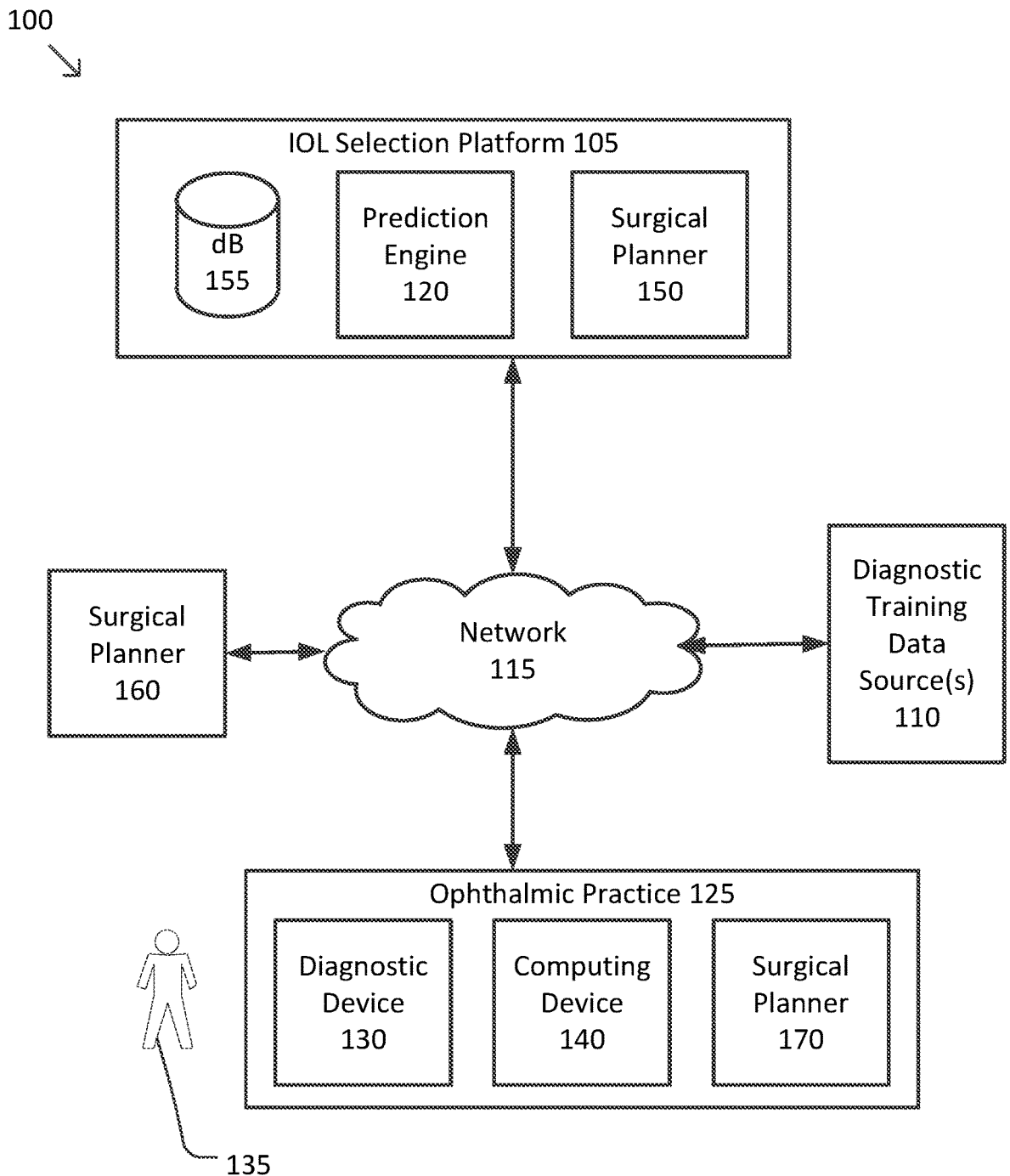
FIG. 1 is a diagram of a system for IOL selection according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The technology described below involves systems and methods to improve post implantation vision for a patient by determining an appropriate intraocular lens (IOL) power of an intraocular lens for implanting into the patient's eyes based on a target (e.g., desired) post-operative manifest refraction in spherical equivalent (MRSE). The systems and methods use a two-stage process to determine the appropriate IOL power for the patient. During the first stage, data associated with a current IOL implantation such as one or more pre-operative measurements of the patient's eyes may be obtained. From a database storing multiple historical IOL implantation records associated with previously performed IOL implantations (also referred to as historical IOL implantations), a subset of historical IOL implantation records that are most similar to the current IOL implantation may be selected. During the second stage, multiple prediction models that estimate the post-operative MRSE may be evaluated to identify a prediction model having a smallest deviation based on the selected subset of historical IOL implantation records. The identified prediction model may be used to generate estimated post-operative MRSE values based on a set of available IOL powers. An available IOL power corresponding to an estimated post-operative MRSE value that matches the target post-operative MRSE may be selected. An intraocular lens corresponding to the selected IOL power may then be used for implantation in the patient's eyes.

FIG. 1 illustrates a system 100 for IOL selection according to some embodiments. System 100 includes an IOL selection platform 105 coupled with one or more diagnostic training data sources 110 via a network 115. In some examples, network 115 may include one or more switching devices, routers, local area networks (e.g., an Ethernet), wide area networks (e.g., the Internet), and/or the like. Each of the diagnostic training data sources 110 may be a database, a data repository, and/or the like made available by an, ophthalmic surgery practice, an eye clinic, a medical university, an electronic medical records (EMR) repository, and/or the like. Each of the diagnostic training data sources 110 may provide IOL selection platform 105 with training data in the form of one or more of multi-dimensional images and/or measurements of patients' pre- and post-operative eyes, surgical planning data, surgical console parameter logs, surgeon identification data, diagnostic device data, patient demographical data, surgical complication logs, patient medical history, patient demographic data, information on an implanted IOL, and/or the like. IOL selection platform 105 may store the training data in one or more databases 155 which may be configured to anonymize, encrypt, and/or otherwise safeguard the training data.

IOL selection platform 105 includes a prediction engine 120 which may (as explained in greater detail below) process the received training data, extract measurements of an eye, perform raw data analysis on the training data, train machine learning algorithms and/or models to estimate a post-operative MRSE based on the pre-operative measurements, and iteratively refine the machine learning to optimize the various models used to predict the post-operative MRSE to improve their use with future patients to improve their post-operative vision outcomes (e.g., better optical properties of the eye with the implanted IOL). In some examples, prediction engine 120 may evaluate multiple models (e.g., one or more neural networks) that are trained to select one model for determining an appropriate IOL power for a patient.

IOL selection platform 105 is further coupled, via network 115, to one or more devices of an ophthalmic practice 125. The one or more devices include a diagnostic device 130. Diagnostic device 130 is used to obtain one or more multi-dimensional images and/or other measurements of an eye of a patient 135. Diagnostic device 130 may be any of a number of devices for obtaining multi-dimensional images and/or measurements of ophthalmic anatomy such as an optical coherence tomography (OCT) device, a rotating camera (e.g., a Scheimpflug camera), a magnetic resonance imaging (MM) device, a kerometer, an ophthalmometer, an optical biometer, and/or the like.

The ophthalmic practice 125 may also include one or more computing devices 140 for obtaining data associated with a current IOL implantation. For example, the one or more computing devices 140 may obtain, from the diagnostic device 130, the multi-dimensional images and/or measurements of patient 135. In some embodiments, the one or more computing devices 140 may also obtain device configuration data associated with the diagnostic device 130. For example, the one or more computing devices 140 may obtain a model number of the diagnostic device 130 and a software release number of a software installed in the diagnostic device 130. In some embodiments, the one or more computing devices 140 may also obtain other information, such as an identity of the surgeon assigned to perform the IOL implantation for patient 135, an ethnicity of patient 135, a gender of patient 135, a height of patient 135, and an age of patient 135, for example, through a user interface of the one or more computing device 140. The one or more computing devices 140 may send the obtained one or more multi-dimensional images and/or measurements of patient 135, device configuration data associated with the diagnostic device 130, the surgeon identity data, and demographic data of patient 135 to IOL selection platform 105. The one or more computing devices 140 may be one or more of a stand-alone computer, a tablet and/or other smart device, a surgical console, a computing device integrated into the diagnostic device 130, and/or the like.

IOL selection platform 105 may receive biometric data of patient 135 (e.g., measurements of patient 135, and/or compute values from the measurements), and generate an estimate of the post-operative MRSE for various IOL types and IOL powers using prediction engine 120. Prediction engine may then be used to help select an IOL type and IOL power for patient 135 by providing ophthalmic practice 125 and/or a surgeon or other user with the estimated post-operative MRSE for the various IOL types and IOL powers.

Diagnostic device 130 may further be used to obtain post-operative measurements of patient 135 after the patient 135 undergoes cataract removal and IOL implantation using the selected IOL. The one or more computing devices 140 may then send the post-operative multi-dimensional images and/or measurements of patient 135 and the selected IOL to IOL selection platform 105 for use in iteratively training and/or updating the models used by prediction engine 120 so as to incorporate information from patient 135 for use with future patients.

The estimated post-operative MRSE, selected IOL, and/or selected IOL power may be displayed on computing device 140 and/or another computing device, display, surgical console, and/or the like. Additionally, IOL selection platform 105 and/or the one or more computing devices 140 may identify in the measurements various characteristics of the anatomy of patient 135, as explained below in more detail. Further, IOL selection platform 105 and/or one or more computing devices 140 may create graphical elements that identify, highlight, and/or otherwise depict the patient anatomy and/or the measured characteristics. IOL selection platform 105 and/or the one or more computing devices 140 may supplement the measurements with the graphical elements.

In some embodiments, IOL selection platform 105 may further include a surgical planner 150 that may be used to provide one or more surgical plans to ophthalmic practice 125 that uses the estimated post-operative MRSE, the selected IOL, and/or the selected IOL power.

In some embodiments, system 100 may further include a stand-alone surgical planner 160 and/or ophthalmic practice 125 may further include a surgical planner module 170 on the one or more computing device 140.

As discussed above and further emphasized here, FIG. 1 is merely an example which should not unduly limit the scope of the claims. One of ordinary skill in the art would recognize many variations, alternatives, and modifications. According to some embodiments, IOL selection platform 105 and/or one or more components of IOL selection platform 150, such as databases 155, prediction engine 120, and/or surgical planner 150, may be integrated into the one or more devices of ophthalmic practice 125. In some examples, computing device 140 may host IOL selection platform 105, databases 155, prediction engine 120, and/or surgical planner 150. In some examples, surgical planner 150 may be combined with surgical planner 170.

Figure 2A:
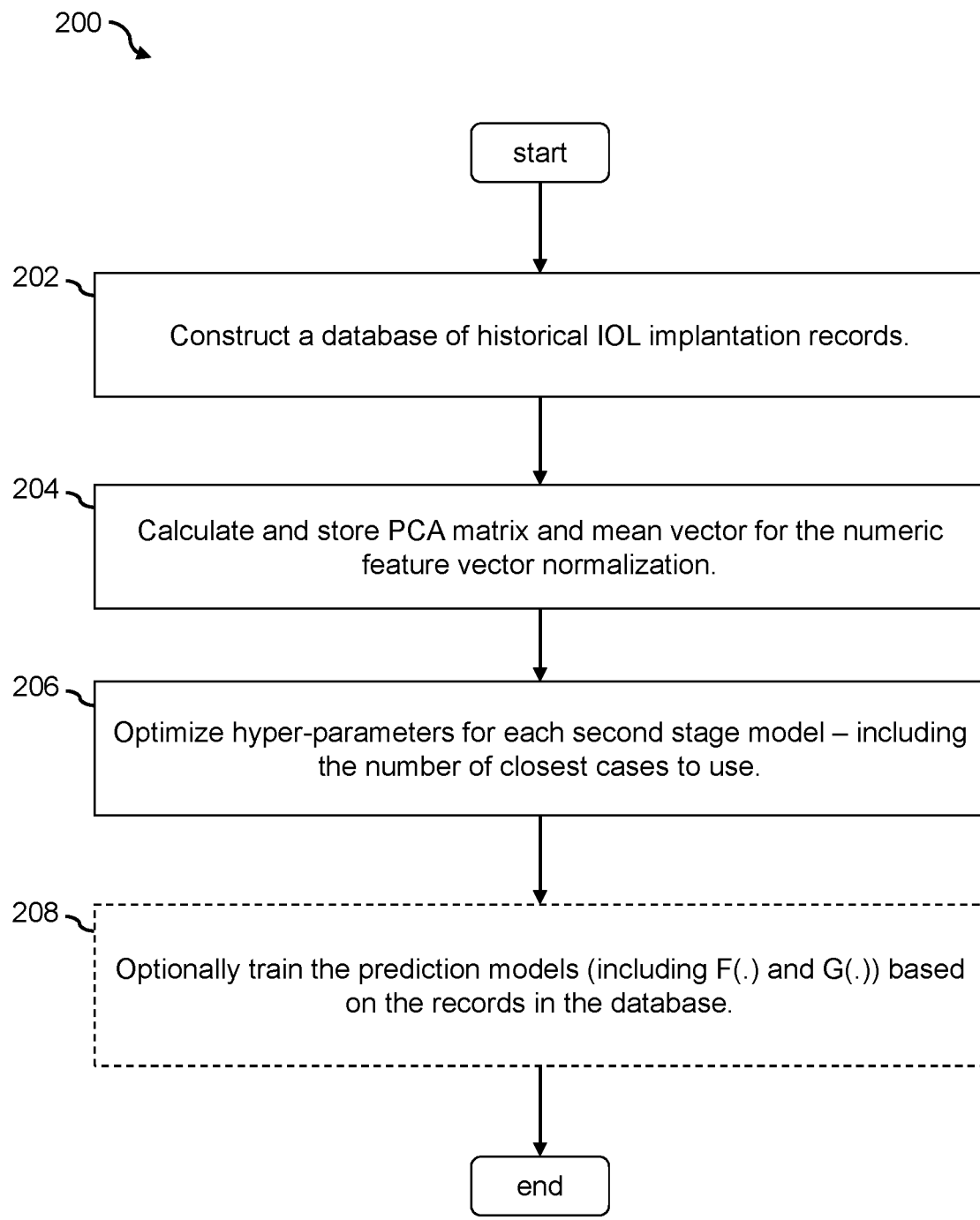
FIG. 2A is a diagram of a method of developing a database for use in implanting an IOL according to some embodiments.

FIG. 2A is a diagram of a method 200 of developing a database for use in selecting an IOL power and implanting an IOL according to some embodiments. One or more of the processes 202-208 of method 200 may be implemented, at least in part, in the form of executable code stored on non-transitory, tangible, machine-readable media that when run by one or more processors (e.g., the processors of prediction engine 120, IOL prediction platform, diagnostic device 130, the one or more computing devices 140, and/or one or more of the surgical planners 150, 160, and/or 170) may cause the one or more processors to perform one or more of the processes 202-208. According to some embodiments, process 208 is optional and may be omitted.

At a process 202, a database of historical IOL implantation records is constructed. For example, prediction engine 120 may obtain training data from the diagnostic training data source(s) 110 and store the training data in database 155. The training data may correspond to previously performed IOL implantation cases (also referred to as "historical IOL implantations"). In some embodiments, prediction engine 120 may organize the database 155 based on the historical IOL implantation cases such that each record in the database 155 contains the training data associated a particular historical IOL implantation. The training data in each record may include both categorical data and numerical data. The categorical data in each record may include information such as an IOL model number, an identification of a surgeon who performed the IOL implantation, a gender of the patient, an ethnicity of the patient, device configuration data associated with the biometric instrument used to obtain the eye measurement data of the patient (e.g., model number and software release number, etc.). The numerical data in each record may include pre-operative eye measurements (e.g., a corneal power, an axial length, a corneal thickness, an anterior chamber depth, a white-to-white distance, a pre-operative MRSE, etc.), an age of the patient, and a height of the patient. Furthermore, each historical IOL implantation record may include an actual IOL power selected for the case and the resulting actual post-operative MRSE. Both the IOL power and the post-operative MRSE may include quantized numerical data and can be treated by prediction engine 120 as numerical data or categorical data.

In some examples, IOL power is typically known to the nearest 0.25 or 0.5 diopters (d) and the postoperative MRSE is generally known to the nearest 0.125 d.

At a process 204, a principal components analysis (PCA) matrix and mean vector are calculated and stored for the numeric feature vector normalization. For example, prediction engine 120 may normalize the numeric data in the historical IOL implantation records such that different numerical features may carry proportional weight (e.g., the same weight as each other) when the historical IOL implantation records are compared against each other, or against a current IOL implantation. Different embodiments use different techniques to normalize the numerical data. In some embodiments, prediction engine 120 generates a numerical feature vector for each record and uses PCA to compute a linear transform to decorrelate and normalize the numerical feature vectors. A numerical features vector for a historical IOL implantation record may include some or all of the numerical values included in the record. An example numerical feature vector for a record may be expressed using Equation 1.

$$x_n = \begin{bmatrix} \text{Corneal power} \\ \text{Axial length} \\ \text{Corneal thickness} \end{bmatrix} \quad (1)$$

Where $x_n$ represents the numerical feature vector (also referred to as an "input feature vector") for the $n^{th}$ record in the database.

While the expression illustrated above includes only three numerical features, more features or other combinations of features may be included in a numerical feature vector in some embodiments.

To perform PCA, the means of the numerical feature vector components may be calculated using Equation 2.

$$m_j = \frac{1}{M}\sum_{i=0}^{M-1} x_{i,j} \text{ for } j = 0, 1, \ldots, N-1 \quad (2)$$

Where i is the historical IOL implantation record index, j is the numerical feature index, $m_j$ is the mean of element j from the numerical feature vectors, M is the number of historical IOL implantation records in the database 155, N is the number of dimensions in the numerical features vector (e.g., the number of numerical features in each vector, which is 3 in the case of Equation 1), and $x_{i,j}$ is the feature value for the numerical feature indicated by the numerical feature index j for the historical IOL implantation record indicated by the record index i.

A covariance matrix C with elements $C_{j,k}$ may then be calculated for each mean of the numerical feature vectors by prediction engine 120 using Equation 3.

$$c_{j,k} = \sum_{i=0}^{M-1} (x_{i,j} - m_j)(x_{i,k} - m_k) \quad (3)$$

Where i is the historical IOL implantation record index in the database 155, j,k is the covariance matrix element indices, both in the range of 0, 1, ..., N−1, $m_j$ is the mean of element j from the numerical features vectors, M is the number of historical IOL implantation records in the database 155, N is the number of dimensions in the numerical feature vector (e.g., the number of numerical features in each vector), and $x_{i,j}$ is the feature value for the numerical feature indicated by the numerical feature index j for the historical IOL implantation record indicated by the record index i.

Next, a lower triangular matrix L may be calculated by prediction engine 120 such that $LL^T=C$. The matrix square root may be calculated, for example, using Cholesky decomposition. Finally, a lower triangular inverse of a covariance square root matrix $M=L^{-1}$ may be calculated by prediction engine 120 using a numerical linear algebra technique. To apply the PCA transformation to a numerical feature vector, prediction engine 120 of some embodiments may subtract the calculated mean vector (e.g., m) from the input numerical feature vector, and multiply the result by M, as shown in Equation 4.

$$y=M(x-m) \quad (4)$$

Where y is the output normalized feature vector, M is the lower triangular inverse of a covariance square root matrix, x is the input non-normalized features vector, and m is the mean vector.

At a process 206, one or more hyper-parameters for the two-stage process to determine the appropriate IOL power for a patient may be determined. As discussed above, during the first stage of the two-stage process, a subset of historical IOL implantation records that is closest to a current IOL implantation is selected from the database. Thus, prediction engine 120 may determine a number of records (e.g., 70, 100, 400, etc.) (also referred to as a "hyper-parameter K") to be selected such that the subset of historical IOL implantation records is limited to the determined number K. Furthermore, for prediction models that are implemented using a deep neural network, prediction engine 120 may also determine a number of hidden layers for those prediction models. The hyperparameters may be determined offline and prior to the training (e.g., learning) of the prediction models. In some embodiments, prediction engine 120 may determine (e.g., optimize) the hyper-parameters using a brute force approach to test over a predetermined range of hyperparameters. For example, to determine the number of records to be selected during the first stage of the two-stage process (the hyper-parameter K), prediction engine 120 may test each number within a range (e.g., 50-100, 20-200, etc.). To determine the number of hidden layers in the neural network, prediction engine 120 may test each number of hidden layers within a range (e.g., 1-5, 2-10, etc.).

In some embodiments, prediction engine 120 may employ three data sets to perform such optimization. For example, the historical IOL implantation records in the database 155 may be split by prediction engine 120 into three sets—a training set, a validation set, and a testing set. The distribution of the three sets may vary but the training set may include a larger percentage than the validation set and the testing set. An example distribution may include 60% of the historical IOL implantation records as the training set, 20% of the remaining historical IOL implantation records as the validation set and the remaining 20% of the historical IOL implantation records as the testing set. As an example, an historical IOL implantation database of 20,000 records can be split by prediction engine 120 into 12,000 training cases, 4,000 validation cases, and 4,000 testing cases. For that collection of 20,000 records, prediction engine 120 may determine that an optimal number of records to be selected during the first stage of the two-stage process (the hyper-parameter K) to be around 100 using the techniques disclosed above. However, for another database containing different historical IOL implantation records and/or a different number of historical IOL implantation records, prediction engine 120 may determine another optimal number of records to be selected (another hyper-parameter K).

In some embodiments, prediction engine 120 may perform an exhaustive search over the hyper-parameters within the determined range. For example, for each hyper-parameter value (e.g., for each number of records to be selected within the range, for each number of hidden layers within the range, etc.), prediction engine 120 may use the hyper parameter value to train the prediction models using the training set. The trained prediction models are then evaluated by prediction engine 120 using the validation set, while the validation results for the hyper-parameter values are recorded. After evaluating all hyper-parameter values within the range(s), embodiments of prediction engine 120 may perform a final estimate of the generalization performance using the testing set. Under this brute force approach, the optimization of hyper-parameters may take a long time, especially when the number of hyper-parameter values to search over is large. Thus, prediction engine 120 may perform the hyper-parameter optimization offline prior to performing the two-stage process.

At a process 208, prediction models may be trained optionally based on the records in the database. In some embodiments, multiple prediction models may be available for use by prediction engine 120 during the second stage of the two-stage process. The different prediction models may use different prediction techniques (e.g., regression techniques). For example, the prediction models that are available for use by prediction engine 120 may include models that use at least one of the following regression techniques: multiple linear regression, multiple polynomial regression, K-Nearest Neighbors with radial basis functions, neural networks, and other suitable regression techniques.

In some embodiments, the prediction models that are available to prediction engine 120 includes two types of prediction models. A first type of prediction models (also referred to as F(.) models) generates a theoretical IOL power value based on a set of numerical feature data (e.g., a numerical feature vector) and a target post-operative MRSE. An F(.) model may be expressed according to Equation 5.

$$IOL = F(x, T) \quad (5)$$

Where x is the input vector of numeric features, T is the target post-operative MRSE, and IOL is the theoretical IOL power value that would yield the target post-operative target refraction T based on biometric data of a patient included in the input vector x.

A second type of models (also referred to as G(.) models) estimates (e.g., predicts) a post-operative MRSE of a patient based on a set of numerical features associated with the patient (e.g., a numerical feature vector) and a selected IOL power. A G(.) model may be expressed according to Equation 6.

$$R_x = G(x, SIOL) \quad (6)$$

Where x is the input vector of numeric features, SIOL is the selected IOL power, and $R_x$ is the estimated post-operative MRSE.

In some embodiments, prediction engine 120 may train the prediction models available for use during the second stage of the two-stage process using the historical IOL implantation records stored in the database 155 offline prior to performing the two-stage process. For example, prediction engine 120 may train prediction models of both types (the F(.) models and the G(.) models) using the historical IOL implantation records stored in the database 155.

Figure 2B:
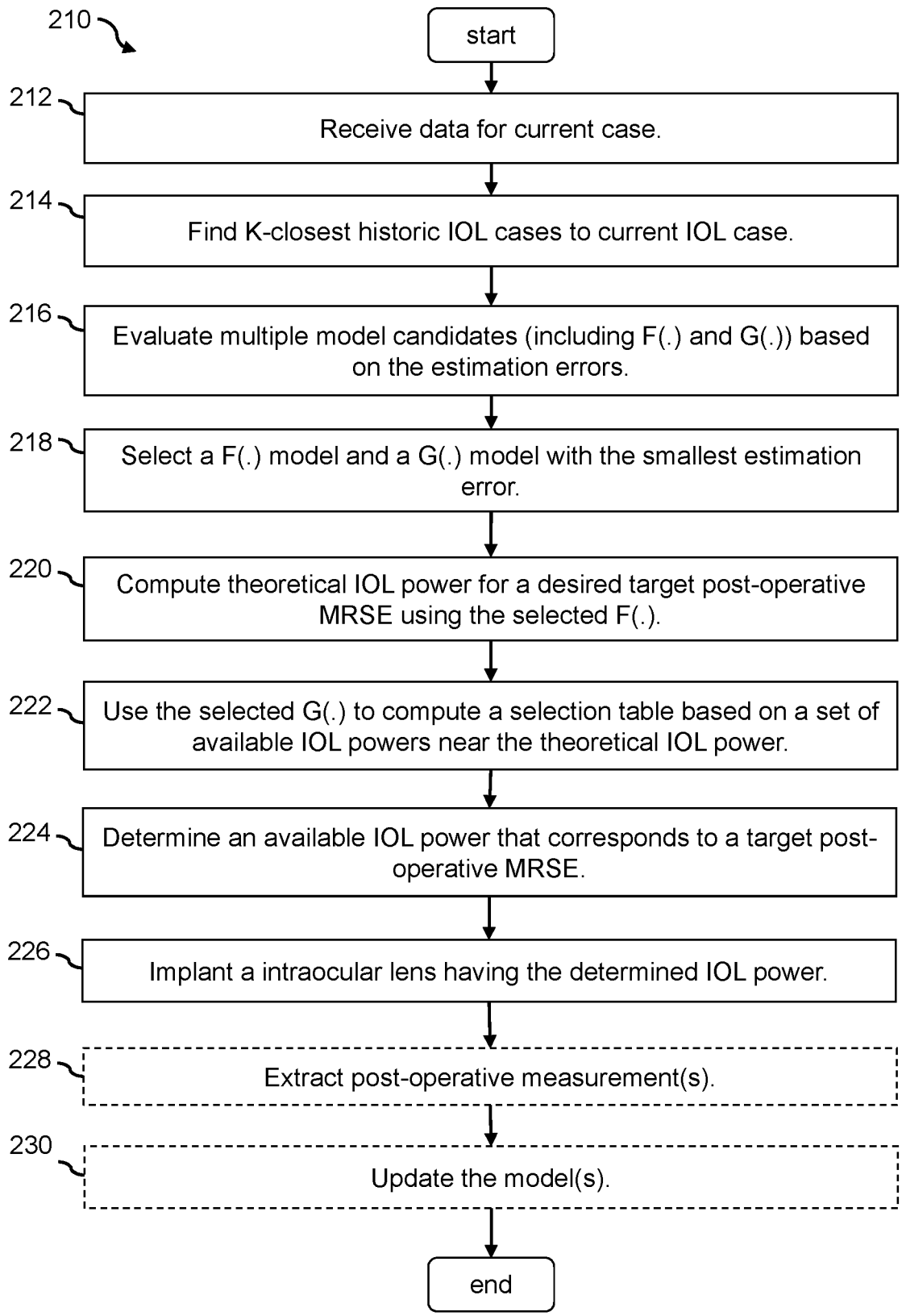
FIG. 2B is a diagram of a method of performing a two-stage process for implanting an IOL according to some embodiments.

FIG. 2B is a diagram of a method 210 of performing the two-stage process for implanting an IOL for a patient according to some embodiments. One or more of the processes 212-230 of method 210 may be implemented, at least in part, in the form of executable code stored on non-transitory, tangible, machine-readable media that when run by one or more processors (e.g., the processors of prediction engine 120, IOL prediction platform, diagnostic device 130, the one or more computing devices 140, and/or one or more of the surgical planners 150, 160, and/or 170) may cause the one or more processors to perform one or more of the processes 212-230. According to some embodiments, processes 228 and/or 230 are optional and may be omitted.

Figure 3:
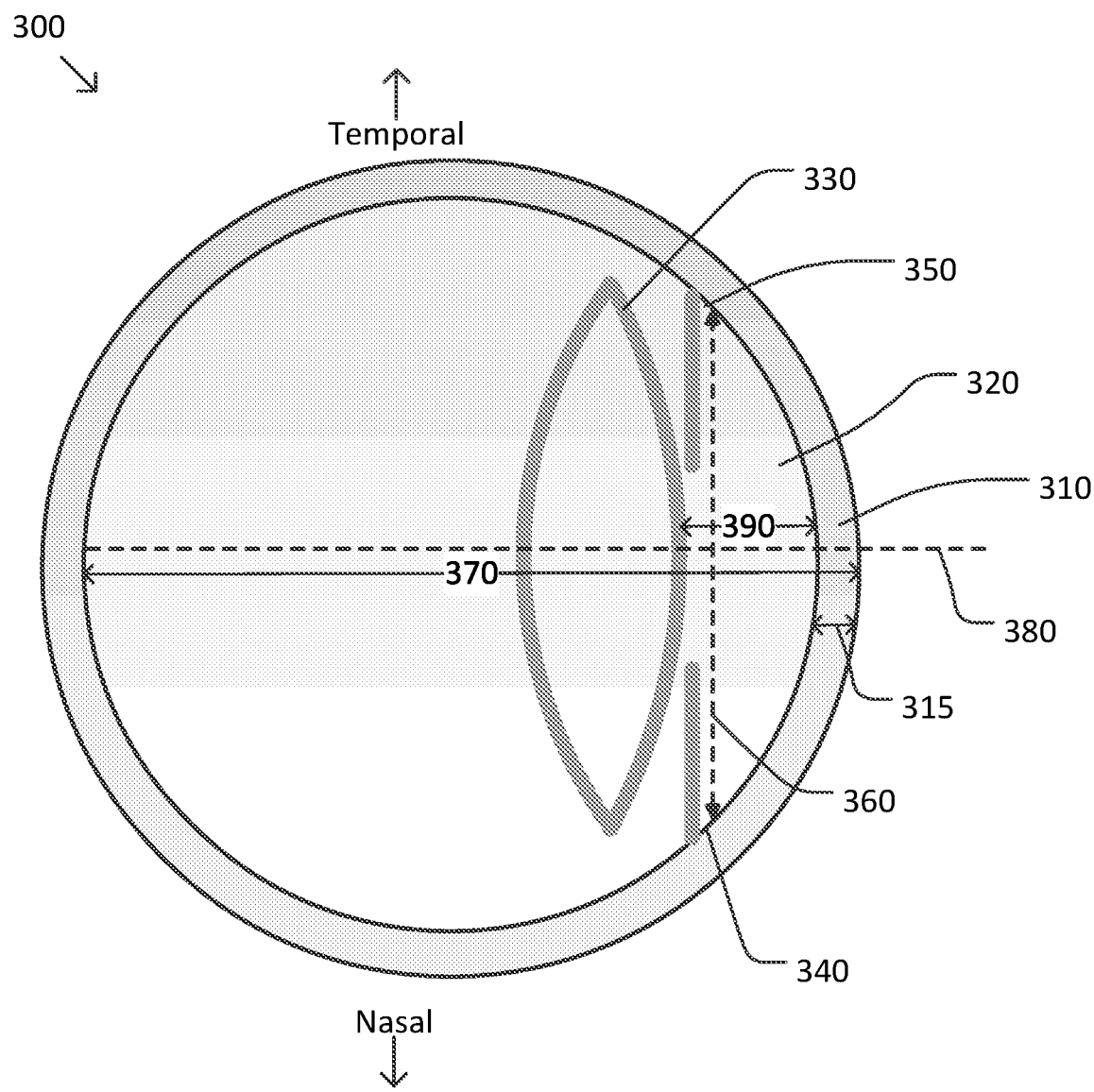
FIG. 3 is a diagram of an eye and characteristics of the eye according to some embodiments.

At a process 212, data associated with a current IOL implantation case may be received. For example, prediction engine 120 may obtain one or more pre-operative measurements of an eye of the patient from diagnostic device 130. In some embodiments, one or more of the pre-operative eye measurements may be extracted from one or more pre-operative images of the eye of patient 135 obtained using a diagnostic device, such as diagnostic device 130, an OCT device, a rotating (e.g., Scheimpflug) camera, an MM device, and/or the like. In some examples, one or more of the pre-operative measurements may be determined using one or more measuring devices, such as diagnostic device 130, a keratometer, an ophthalmometer, an optical biometer, and/or the like. Process 210 is described in the context of FIG. 3, which is a diagram of an eye 300 and characteristics of the eye according to some embodiments. As shown in FIG. 3, eye 300 includes a cornea 310, an anterior chamber 320, and a lens 330.

In some embodiments, one measurement of interest for eye 300 is the white-to-white diameter of cornea 310. In some examples, the white-to-white diameter of cornea 310 may be measured using an optical biometer. In some examples, the white-to-white diameter of cornea 310 may be determined by analyzing one or more images of eye 300, for example, by measuring a distance between the sclera of the eye.

In some embodiments, one measurement of interest for eye 300 is the average keratometry or roundness of the anterior surface of cornea 310. In some examples, the average keratometry of cornea 310 may be measured using the one or more images of eye 300, a keratometer, and/or the like. In some examples, the average keratometry of cornea 310 may be base based on an average of the steep keratometry and the shallow keratometry measurements of cornea 310. In some examples, the average keratometry of cornea 310 may be expressed as a radius of curvature (rc) of cornea 310, which is 337.5 divided by the average keratometry.

In some embodiments, one measurement of interest from eye 300 is the axial length 370 of eye 300 as measured from the anterior surface of cornea 310 to the retina along central axis 380 of eye 300. In some examples, axial length 370 may be determined using the one or more images of eye 300, biometry of the eye, and/or the like.

In some embodiments, one measurement of interest from eye 300 is a pre-operative anterior chamber depth (ACD) 390 of the eye corresponding to the distance between the posterior surface of cornea 310 and the anterior surface of the pre-operative lens 330. In some examples, axial length 370 may be determined using the one or more images of eye 300, biometry of the eye, and/or the like.

In some embodiments, one measurement of interest from eye 300 is the corneal thickness 315 of eye 300 as measured from the posterior surface of cornea 310 to the anterior surface of cornea 310 along central axis 380 of eye 300. In some examples, corneal thickness 315 may be determined using the one or more images of eye 300, biometry of the eye, and/or the like.

In some embodiments, in addition to obtaining measurements of the eye of patient 135, other circumstantial data associated with the current IOL implantation may also be obtained. For example, the one or more computing devices 140 may obtain, from the diagnostic device 130, device configuration data associated with the diagnostic device 130 that provided the measurements of the eye of patient 135. The device configuration data may include a model number of the diagnostic device 130 and a software release number of a software installed in the diagnostic device 130. In some examples, the one or more computing devices 140 may obtain the configuration data by communicating with the diagnostic device 130 using an application programming interface (API) of the diagnostic device 130. Furthermore, the one or more computing devices 140 may also obtain other information related to the current IOL implantation for patient 135, such as an identity of the surgeon assigned to perform the IOL implantation for patient 135, an ethnicity of patient 135, a gender of patient, a height of patient 135, and an age of patient 135. In some embodiments, the one or more computing devices 140 may provide a user interface that enables a user to provide the surgeon identity and the patient demographic data. The one or more computing devices 140 may then send the biometric data and the environmental data to IOL selection platform 105.

Referring back to FIG. 2, at a process 214, a subset of historical IOL implantation records (e.g., K-closest records) may be selected based on the obtained data. As discussed above, the database 155 of IOL selection platform 105 may store training data obtained from diagnostic training data source(s) 110. The training data may include data related to IOL implantations performed previously for other patients (e.g., historical IOL implantations). Specifically, each record in the database 155 may include numerical data and categorical data related to a particular historical IOL implantation. The numerical data in each record may include pre-operative eye measurements such as a corneal power, an axial length, a corneal thickness, an anterior chamber depth, a white-to-white distance, a pre-operative MRSE, etc.), an age of the patient, a height of the patient, and/or the like. In some embodiments, the numerical data stored in each record may be normalized using the techniques discussed above with respect to process 204, and may be stored as a numerical feature vectory. The categorical data in each record may include information such as an IOL model number, an identification of a surgeon who performed the IOL implantation, a gender of the patient, an ethnicity of the patient, device configuration data associated with the biometric instrument used to obtain the eye measurement data of the patient (e.g., model number and software release number, etc.), and/or the like. Furthermore, each historical IOL implantation record may include an actual IOL power selected for the case and the resulting actual post-operative MRSE.

In some embodiments, prediction engine 120 may select a subset of historical IOL implantation records from the database 155 that are most similar to the current IOL implantation for the patient 135 based on the obtained biometric data and/or environmental data. The selected subset of historical IOL implantation records may include (and may be limited to) a number of records corresponding to the predetermined hyper-parameter K (e.g., determined at the process 206). In some embodiments, prediction engine 120 may use a K-Nearest Neighbor (KNN) algorithm to select the subset of records from the database 155 that are closest to the current IOL implantation using the predetermined hyper-parameter K as a K parameter for the KNN algorithm. For example, prediction engine 120 may first generate a numerical feature vector for the current IOL implantation based on some or all of the numerical data (e.g., pre-operative eye measurements of patient 135, an age of patient 135, a height of patient 135, etc.). The numerical features included in the numerical feature vector generated for the current IOL implantation may correspond to the features included in the pre-generated numerical feature vectors associated with the historical IOL implantation records stored in the database 155. In some examples, the numerical feature vector may include a pre-operative corneal power of an eye of patient 135, an axial length of the eye of patient 135, and a corneal thickness of the eye of patient 135, such as is shown in Equation 1. Prediction engine 120 may then normalize the components in the numerical feature vector generated for the current IOL implantation using the techniques discussed above, for example, using Equation 4.

The normalized vectors may be used to calculate the Euclidean distances between the current IOL implantation and each of the historical IOL implantation records in the database 155. The Euclidean distance between vectors a and b with elements $a_i$ and $b_i$, respectively, may be calculated by prediction engine 120 using Equation 7.

$$d = \sqrt{\sum_{i=0}^{N-1}(a_i - b_i)^2} \qquad (7)$$

Based on the calculated Euclidean distances, prediction engine 120 may then select the predetermined number of historical IOL implantation records (e.g., K number of records) having the smallest distance values for use in the second stage of the two-stage process.

After selecting the subset of historical IOL implantation records, at a process 216, multiple prediction model candidates may be evaluated based on the selected subset of historical IOL implantation records. As discussed above, multiple prediction models (including F(.) models and G(.) models) may be available for use by prediction engine 120 during the second stage of the two-stage process. Prediction engine 120 may use these prediction models as model candidates for selecting one or more model(s) for use during the second stage of the two-stage process based on their performances. If the prediction models were not trained offline (e.g., process 208 was not performed), prediction engine 120 may train the available prediction models using the historical IOL implantation records in the database 155 at this time. In some embodiments, prediction engine 120 may use only the selected subset of historical IOL implantation records to train the prediction models.

In some embodiments, prediction engine 120 may evaluate the F(.) models by using each of the F(.) models to generate theoretical IOL powers based on the numerical feature data (e.g., the numerical feature vectors) associated with the selected subset of historical IOL implantation records. Prediction engine 120 may then generate a performance score for each of the F(.) models based on deviations between the theoretical IOL powers generated by the F(.) model and the actual IOL powers used indicated in the subset of historical IOL implantation records. For example, the performance score for each of the F(.) models may be generated based on at least one of a mean error, a standard deviation error, a mean absolute error (MAE), a standard deviation of absolute error, a percentage with MAE less than a predetermined value (e.g., 0.5, 1.0, etc.), and a percentage of estimations that are within a range having a predetermined confidence (e.g., 95%).

In some embodiments, prediction engine 120 may also evaluate the G(.) models by using each of the G(.) models to estimate (e.g., predict) post-operative MRSE values based on the numerical feature data (e.g., the numerical feature vectors) and the actual IOL powers used in the selected subset of historical IOL implantation records. Prediction engine 120 may then generate a performance score for each of the G(.) models based on deviation between the estimated post-operative MRSE values generated by the G(.) model and the actual post-operative MRSE values indicated in the subset of historical IOL implantation records. For example, an estimation error (e.g., deviation) between an estimated post-operative MRSE generated by the G(.) model and the actual post-operative MRSE indicated in a given historical IOL implantation record n may be expressed according to Equation 8.

$$e[n] = ARx[n] - Rx[n] \tag{8}$$

Where n is the record index of a historical IOL implantation record from the selected subset of historical IOL implantation records, ARx[n] is the actual post-operative MRSE indicated in the historical IOL implantation record having a record index n, Rx[n] is the post-operative MRSE estimated by the G(.) model, and e[n] is the estimation error for the record n.

In some embodiments, the performance score for each of the G(.) models may be generated based on at least one of a mean error, a standard deviation error, a mean absolute error (MAE), a standard deviation of absolute error, a percentage with MAE less than a predetermined value (e.g., 0.5, 1.0, etc.), and a percentage of estimations that are within a range having a predetermined confidence (e.g., 95%). For example, based on Equation 8 above, the performance score for a given G(.) model that is based on an estimation error standard deviation may be expressed according to Equation 9.

$$SD = \sqrt{\frac{1}{K}\sum_{n=0}^{K-1}(e[n])^2 - \left(\frac{1}{K}\sum_{n=0}^{K-1}e[n]\right)^2} \tag{9}$$

Where n is the record index of a historical IOL implantation record from the selected subset of historical IOL implantation records, K is the number of records included in the selected subset of historical IOL implantation records, e[n] is the estimation error for the record n calculated using Equation 8, and SD is the estimation error standard deviation for the G(.) model.

At a process 218, a F(.) model and a G(.) model may be selected from the model candidates. For example, prediction engine 120 may select a F(.) model and a G(.) model from the model candidates based on the performance scores generated for the model candidates. In some embodiments, prediction engine 120 may select a F(.) model having the best performance score (e.g., indicating a lowest standard deviation) among the F(.) model candidates and may select a G(.) model having the best performance score (e.g., indicating a lowest standard deviation) among the G(.) model candidates.

At a process 220, a theoretical IOL power for a target (e.g., desired) post-operative MRSE for patient 135 in the current IOL implantation may optionally be calculated. For example, prediction engine may use the F(.) model selected in the process 218 to generate a theoretical IOL power based on the numerical feature data associated with patient 135 and a predetermined target post-operative MRSE for patient 135. The target post-operative MRSE may be determined by a surgeon assigned to perform the current IOL implantation for patient 135. The generated IOL power represents the IOL power required for an intraocular lens implanted in the eye of patient 135 in order for patient 135 to achieve the post-operative MRSE after the implantation.

At a process 222, the selected G(.) model is used to compute a selection table based on a set of available IOL powers near the theoretical IOL Power. A set of IOL powers may be available to a surgeon or a user for performing the current IOL implantation for patient 135. For example, intraocular lenses may be manufactured in various, but limited, IOL powers. In one example, manufacturers of intraocular lenses may produce lenses only according to a limited number of IOL powers. When a theoretical IOL power for the current IOL implantation is not generated (e.g., the process 220 was not performed), prediction engine 120 may use the selected G(.) model (selected in the process 218) to calculate estimated post-operative MRSE values based on the numerical feature data associated with patient 135 for all of the IOL powers available for the current IOL implantation. The result may include a table comprising the available IOL powers and corresponding estimated post-operative MRSE values calculated by the selected G(.) model for patient 135.

Because the number of IOL powers available for the current IOL implantation may be large, in some embodiments, prediction engine 120 may reduce computation (and thereby improving the performance speed of this two-stage process) by estimating the post-operative MRSE for only a subset of the available IOL powers. For example, by performing the process 220, a theoretical IOL power for patient 135 is generated using the selected F(.) model. However, the theoretical power generated by the F(.) model may not be available in the set of powers provided by the manufacturer of a given IOL model, so the surgeon or user must select from the set of available IOL powers. As such, prediction engine 120 may select a subset of available IOL powers that are within a predetermined threshold from the theoretical IOL power generated by the F(.) model for computing the selection table in the process 222.

In some examples, when the generated theoretical IOL power is 20 d, prediction engine 120 may select available IOL powers that are within the range of 18 d and 22 d. Prediction engine 120 may then use the selected G(.) model (selected in the process 218) to calculate estimated post-operative MRSE values based on the numerical feature data associated with patient 135 for only the subset of available IOL powers selected by prediction engine 120 based on the theoretical IOL power generated by the F(.) model. The result may include a table comprising the subset of available IOL powers and corresponding estimated post-operative MRSE values calculated by the selected G(.) model for patient 135.

In some embodiments, in addition to calculating the estimated post-operative MRSE values for the subset of available IOL powers, prediction engine 120 may also generate a predicted MRSE range (e.g. limits) with a predetermined confidence (e.g., 90% confidence, 95% confidence, 98% confidence, etc.) for each estimated MRSE value. The predicted MRSE range may be generated based on the standard deviation calculated for the selected G(.) model using Equation 9 above. For example, a predicted MRSE range with 95% confidence for a particular estimated post-operative MRSE Rx may be expressed according to Equation 10.

$$\text{Predicted MRSE range} = Rx \pm 1.96 SD \quad (10)$$

The predicted MRSE ranges may also be included in the table. Prediction engine 120 and/or surgical planner 150 may transmit the table to the one or more computing devices 140 of the ophthalmic practice 125 over network 115 for display on the one or more computing devices 140 to aid the surgeon or the user in the IOL implantation for patient 135.

At a process 224, an available IOL power that corresponds to a target post-operative MRSE may be determined. For example, in addition to transmitting the table including the available IOL powers and estimated post-operative MRSE values to the one or more computing devices 140, prediction engine 120 may also determine a particular available IOL power for use in the current IOL implantation for patient 135 based on the post-operative MRSE values and/or the predicted MRSE ranges. In some embodiments, prediction engine 120 may determine (e.g., select) a particular available IOL power having a corresponding estimated post-operative MRSE value that is closest to the target post-operative MRSE for patient 135. In some embodiments, prediction engine 120 may determine (e.g., select) a particular available IOL power having a corresponding maximum MRSE value and a minimum MRSE value of the predicted MRSE range that are closest to the target post-operative MRSE for patient 135 (e.g., the smallest deviation from the target post-operative MRSE value, where the deviation is the sum of a difference between the maximum MRSE value and the target post-operative MRSE value and a difference between the minimum MRSE value and the target post-operative MRSE value). Prediction engine 120 and/or surgical planner 150 may transmit the determined particular available IOL power to the one or more computing devices 140 of the ophthalmic practice 125 over network 115 for display on the one or more computing devices 140 to aid the surgeon or the user in the IOL implantation for patient 135.

At a process 226, an intraocular lens having the determined available IOL power is implanted in patient 135. In some examples, an intraocular lens having the IOL power determined during process 224 is implanted in the eye of patient 135 by a surgeon.

At a process 228, one or more post-operative measurements of the eye of patient 135 are obtained. In some examples, the one or more post-operative measurements may include an actual post-operative ACD of the IOL after implantation of the IOL, an actual post-operative MRSE after implantation of the IOL, an actual post-operative emmetropia zone determination, and/or the like. In some examples, the actual post-operative ACD and/or the actual post-operative MRSE may be determined based on one or more images of the post-operative eye, one or more physiological and/or optical measurements of the post-operative eye, and/or the like.

At a process 230, the prediction models available to prediction engine 120 are updated. In some examples, the one or more pre-operative measurements determined during process 212, the actual post-operative ACD, the actual post-operative MRSE and/or the like determined during process 228 may be added in the database 155 as a new historical IOL implantation record and used as additional training data for subsequent training of any of the prediction models. In some examples, the updating may include one or more of updating least-squares fits, feedback to neural networks (e.g., using back propagation), and/or the like. In some examples, one or more of the G(.) models may be trained using one or more loss functions based on their ability to correctly predict the post-operative MRSE for the various candidate IOLs.

Figure 4A:
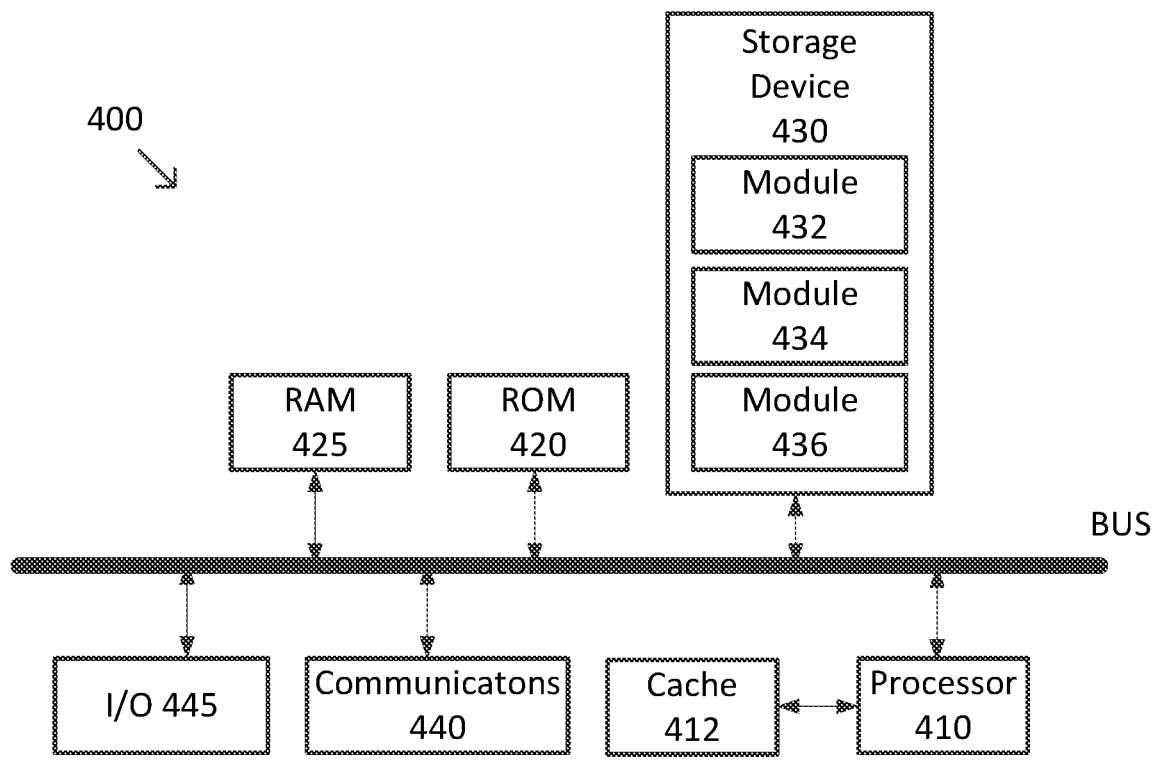
FIGS. 4A and 4B are diagrams of processing systems according to some embodiments.
Figure 4B:
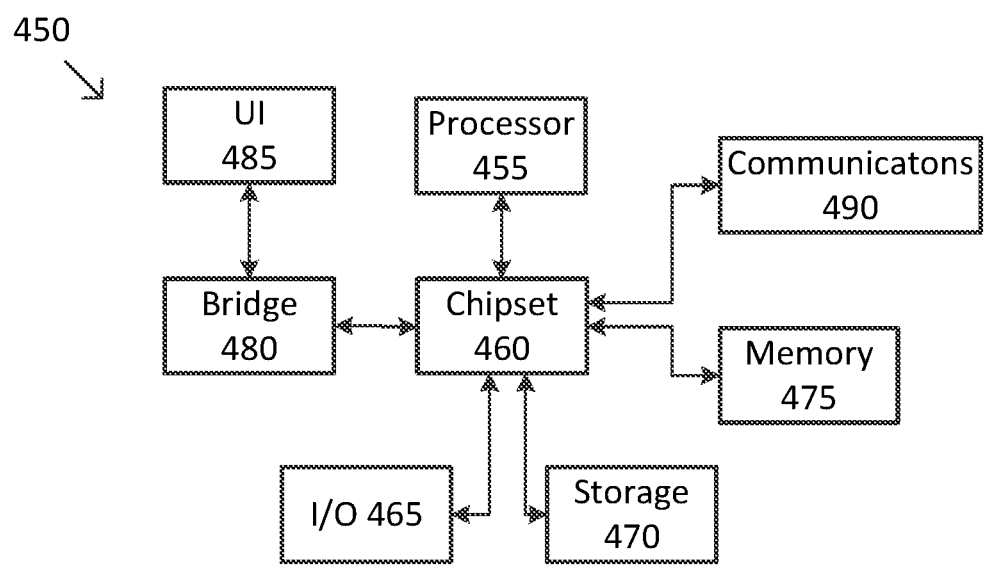

FIGS. 4A and 4B are diagrams of processing systems according to some embodiments. Although two embodiments are shown in FIGS. 4A and 4B, persons of ordinary skill in the art will also readily appreciate that other system embodiments are possible. According to some embodiments, the processing systems of FIGS. 4A and/or 4B are representative of computing systems that may be included in one or more of IOL selection platform 105, ophthalmic practice 125, prediction engine 120, diagnostic device 130, the one or more computing devices 140, any of surgical planner 150, 160, and/or 170, and/or the like.

FIG. 4A illustrates a computing system 400 where the components of system 400 are in electrical communication with each other using a bus 405. System 400 includes a processor 410 and a system bus 405 that couples various system components including memory in the form of a read only memory (ROM) 420, a random access memory (RAM) 425, and/or the like (e.g., PROM, EPROM, FLASH-EPROM, and/or any other memory chip or cartridge) to processor 410. System 400 may further include a cache 412 of high-speed memory connected directly with, in close proximity to, or integrated as part of processor 410. System 400 may access data stored in ROM 420, RAM 425, and/or one or more storage devices 430 through cache 412 for high-speed access by processor 410. In some examples, cache 412 may provide a performance boost that avoids delays by processor 410 in accessing data from memory 415, ROM 420, RAM 425, and/or the one or more storage devices 430 previously stored in cache 412. In some examples, the one or more storage devices 430 store one or more software modules (e.g., software modules 432, 434, 436, and/or the like). Software modules 432, 434, and/or 436 may control and/or be configured to control processor 410 to perform various actions, such as the processes of methods 200 and/or 210. And although system 400 is shown with only one processor 410, it is understood that processor 410 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, system 400 may be implemented as a stand-alone subsystem and/or as a board added to a computing device or as a virtual machine.

To enable user interaction with system 400, system 400 includes one or more communication interfaces 440 and/or one or more input/output (I/O) devices 445. In some examples, the one or more communication interfaces 440 may include one or more network interfaces, network interface cards, and/or the like to provide communication according to one or more network and/or communication bus standards. In some examples, the one or more communication interfaces 440 may include interfaces for communicating with system 400 via a network, such as network 115. In some examples, the one or more I/O devices 445 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 430 may include non-transitory and non-volatile storage such as that provided by a hard disk, an optical medium, a solid-state drive, and/or the like. In some examples, each of the one or more storage devices 430 may be co-located with system 400 (e.g., a local storage device) and/or remote from system 400 (e.g., a cloud storage device).

FIG. 4B illustrates a computing system 450 based on a chipset architecture that may be used in performing any of the methods (e.g., methods 200 and/or 210) described herein. System 450 may include a processor 455, representative of any number of physically and/or logically distinct resources capable of executing software, firmware, and/or other computations, such as one or more CPUs, multi-core processors, microprocessors, microcontrollers, DSPs, FPGAs, ASICs, GPUs, TPUs, and/or the like. As shown, processor 455 is aided by one or more chipsets 460, which may also include one or more CPUs, multi-core processors, microprocessors, microcontrollers, DSPs, FPGAs, ASICs, GPUs, TPUs, co-processors, coder-decoders (CODECs), and/or the like. As shown, the one or more chipsets 460 interface processor 455 with one or more of one or more I/O devices 465, one or more storage devices 470, memory 475, a bridge 480, and/or one or more communication interfaces 490. In some examples, the one or more I/O devices 465, one or more storage devices 470, memory, and/or one or more communication interfaces 490 may correspond to the similarly named counterparts in FIG. 4A and system 400.

In some examples, bridge 480 may provide an additional interface for providing system 450 with access to one or more user interface (UI) components, such as one or more keyboards, pointing/selection devices (e.g., mice, touch pads, scroll wheels, track balls, touch screens, and/or the like), audio devices (e.g., microphones and/or speakers), display devices, and/or the like.

According to some embodiments, systems 400 and/or 460 may provide a graphical user interface (GUI) suitable for aiding a user (e.g., a surgeon and/or other medical personnel) in the performance of the processes of methods 200 and/or 210. The GUI may include instructions regarding the next actions to be performed, diagrams of annotated and/or un-annotated anatomy, such as pre-operative and/or post-operative images of an eye (e.g., such as depicted in FIG. 3), requests for input, and/or the like. In some examples, the GUI may display true-color and/or false-color images of the anatomy, and/or the like.

Figure 5:
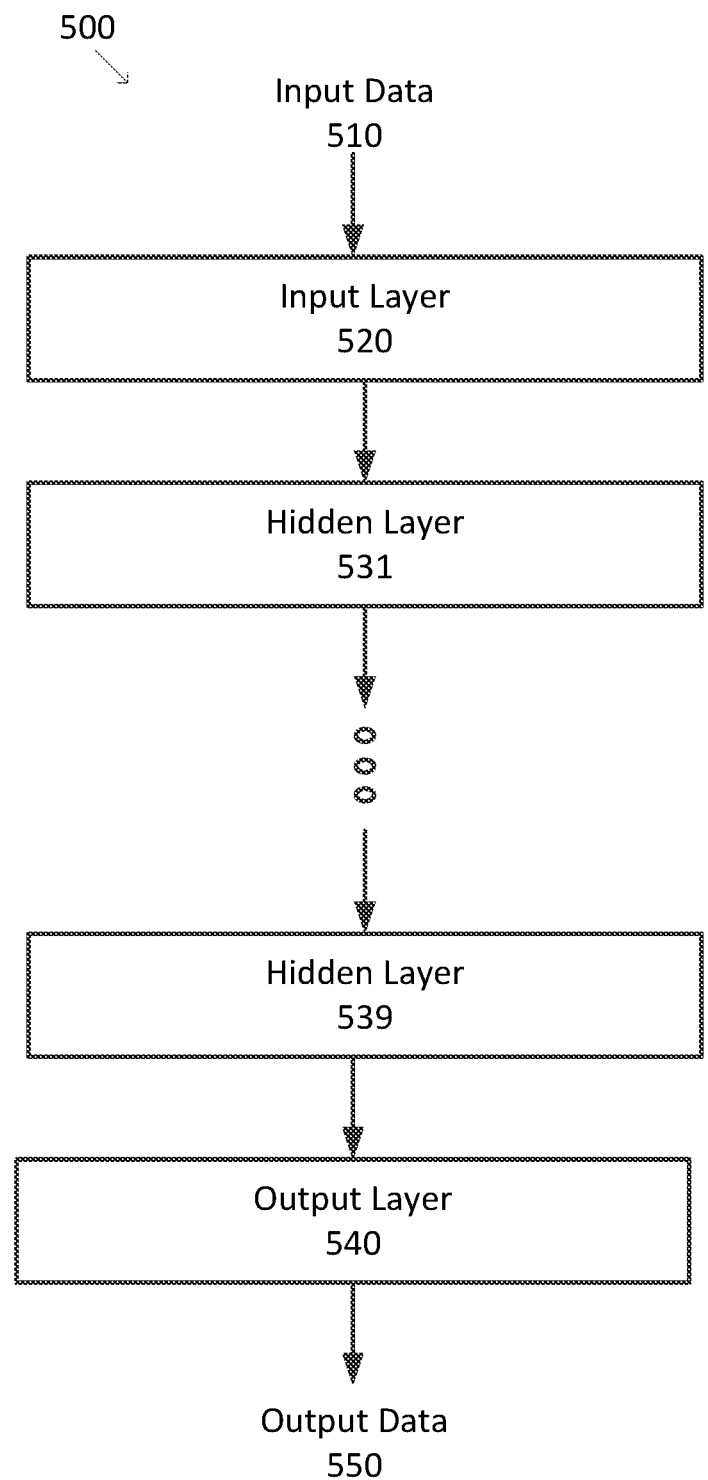
FIG. 5 is a diagram of a multi-layer neural network according to some embodiments.

FIG. 5 is a diagram of a multi-layer neural network 500 according to some embodiments. In some embodiments, neural network 500 may be representative of a neural network used to implement at least some of the prediction models (including the F(.) models and the G(.) models) used by prediction engine 120. Neural network 500 processes input data 510 using an input layer 520. In some examples, input data 510 may correspond to the input data provided to the one or more models and/or the training data provided to the one or more models during the processes 208 and 230 used to train the one or more models. Input layer 520 includes a plurality of neurons that are used to condition input data 510 by scaling, range limiting, and/or the like. Each of the neurons in input layer 520 generates an output that is fed to the inputs of a hidden layer 531. Hidden layer 531 includes a plurality of neurons that process the outputs from input layer 520. In some examples, each of the neurons in hidden layer 531 generates an output that are then propagated through one or more additional hidden layers that end with hidden layer 539. Hidden layer 539 includes a plurality of neurons that process the outputs from the previous hidden layer. The outputs of hidden layer 539 are fed to an output layer 540. Output layer 540 includes one or more neurons that are used to condition the output from hidden layer 539 by scaling, range limiting, and/or the like. It should be understood that the architecture of neural network 500 is representative only and that other architectures are possible, including a neural network with only one hidden layer, a neural network without an input layer and/or output layer, a neural network with recurrent layers, and/or the like.

In some examples, each of input layer 520, hidden layers 531-539, and/or output layer 540 includes one or more neurons. In some examples, each of input layer 520, hidden layers 531-539, and/or output layer 540 may include a same number or a different number of neurons. In some examples, each of the neurons takes a combination (e.g., a weighted sum using a trainable weighting matrix W) of its inputs x, adds an optional trainable bias b, and applies an activation function f to generate an output a as shown in Equation 11. In some examples, the activation function f may be a linear activation function, an activation function with upper and/or lower limits, a log-sigmoid function, a hyperbolic tangent function, a rectified linear unit function, and/or the like. In some examples, each of the neurons may have a same or a different activation function.

$$a = f(Wx+b) \quad (11)$$

In some examples, neural network 500 may be trained using supervised learning (e.g., during processes 208 and 230) where combinations of training data that include a combination of input data and a ground truth (e.g., expected) output data. Differences between the output of neural network 500 as generated using the input data for input data 510 and comparing output data 550 as generated by neural network 500 to the ground truth output data. Differences between the generated output data 550 and the ground truth output data may then be fed back into neural network 500 to make corrections to the various trainable weights and biases. In some examples, the differences may be fed back using a back propagation technique using a stochastic gradient descent algorithm, and/or the like. In some examples, a large set of training data combinations may be presented to neural network 500 multiple times until an overall loss function (e.g., a mean-squared error based on the differences of each training combination) converges to an acceptable level.

Methods according to the above-described embodiments may be implemented as executable instructions that are stored on non-transitory, tangible, machine-readable media. The executable instructions, when run by one or more processors (e.g., processor 410 and/or processor 455) may cause the one or more processors to perform one or more of the processes of methods 200 and/or 210. Some common forms of machine-readable media that may include the processes of methods 200 and/or 210 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method comprising:
   obtaining, by one or more computing devices implementing a prediction engine, one or more pre-operative measurements of an eye for assisting a user to perform an intraocular lens (IOL) implantation in the eye;
   selecting, by the prediction engine from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power;
   evaluating, by the prediction engine, the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records;
   selecting, by the prediction engine, a first prediction model from the first plurality of prediction model candidates based on the evaluating;
   calculating, by the prediction engine using the selected first prediction model, a plurality of estimated post-operative MRSE values based on a set of available IOL powers and the one or more pre-operative measurements of the eye;
   determining, by the prediction engine from the set of available IOL powers, a first IOL power corresponding to a first estimated post-operative MRSE value from the plurality of estimated post-operative MRSE values that matches a predetermined post-operative MRSE value;
   providing, by the prediction engine, the determined first IOL power to the user to aid in selection of an IOL for implantation in the eye;
   obtaining, by the prediction engine, post-operative measurements of the eye including an actual post-operative MRSE value of the eye subsequent to the IOL being implanted in the eye; and
   retraining, by the prediction engine, the selected first prediction model based on the actual post-operative MRSE value, wherein subsequent to the retraining, the retrained first prediction model is configured to be utilized for calculating another plurality of estimated post-operative MRSE values based on the set of available IOL powers and one or more pre-operative measurements of another eye.

2. The method of claim 1, wherein the subset of IOL implantation records is selected to evaluate a second plurality of prediction model candidates, wherein each of the second plurality of prediction model candidates estimates an IOL power based on a set of pre-operative eye measurements and a desired post-operative MRSE, wherein the method further comprises:
   evaluating the second plurality of prediction model candidates based on deviations between estimated IOL powers produced by each of the second plurality of prediction model candidates using eye measurement data in the selected subset of historical IOL implantation records and actual IOL powers indicated in the selected subset of historical IOL implantation records;
   selecting a second prediction model from the second plurality of prediction model candidates based on the evaluating; and
   calculating a second IOL power using the second prediction model based on the predetermined post-operative MRSE value and the one or more pre-operative measurements of the eye.

3. The method of claim 1, further comprising determining the set of available IOL powers from a plurality of IOL powers based on the first IOL power, wherein the set of available IOL powers is within a predetermined threshold from the first IOL power.

4. The method of claim 1, wherein the subset of historical IOL implantation records is limited to a particular number of records, wherein the method further comprises determining the particular number based on an offline analysis of the plurality of historical IOL implantation records.

5. The method of claim 4, wherein the subset of historical IOL implantation records is selected from the plurality of historical IOL implantation records using a K-Nearest Neighbor (KNN) algorithm, wherein a parameter in the KNN algorithm corresponds to the particular number.

6. The method of claim 1, further comprising training the first plurality of prediction model candidates using the plurality of historical IOL implantation records.

7. The method of claim 1, wherein at least two prediction models in the first plurality of prediction model candidates use different types of machine learning algorithms.

8. The method of claim 1, wherein the one or more pre-operative measurements of the eye comprise at least one of a corneal power, an axial length, a corneal thickness, an anterior chamber depth, a white-to-white distance, or a manifest refraction in spherical equivalent.

9. The method of claim 1, further comprising:
   determining, for the first prediction model, a deviation value based on deviations between estimated post-operative MRSEs produced by the first prediction model using eye measurement data in the selected subset of historical IOL implantation records and actual post-operative MRSEs indicated in the selected subset of historical IOL implantation records; and
   determining, for each estimated post-operative MRSE value, a predicted MRSE range based on the deviation value, wherein the first IOL power is determined further based on the predicted MRSE range.

10. The method of claim 1, further comprising implanting an intraocular lens having the first IOL power in the eye.

11. A prediction engine comprising:
    one or more memories comprising executable instructions;

one or more processors in data communication with the one or more memories and configured to execute the instructions, thereby, causing the prediction engine to;
obtain one or more pre-operative measurements of an eye for assisting a user to perform an intraocular lens (IOL) implantation in the eye;
select, from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power;
evaluate the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records;
select a first prediction model from the first plurality of prediction model candidates based on the evaluating;
calculate, using the selected first prediction model, a plurality of estimated post-operative MRSE values based on a set of available IOL powers and the one or more pre-operative measurements of the eye;
determine, from the set of available IOL powers, a first IOL power corresponding to a first estimated post-operative MRSE value from the plurality of estimated post-operative MRSE values that matches a predetermined post-operative MRSE value;
provide, the determined first IOL power to the user to aid in selection of an IOL for implantation in the eye;
obtain post-operative measurements of the eye including an actual post-operative MRSE value of the eye subsequent to the IOL being implanted in the eye; and
retrain the selected first prediction model based on the actual post-operative MRSE value, wherein subsequent to the retraining, the retrained first prediction model is configured to be utilized for calculating another plurality of estimated post-operative MRSE values based on the set of available IOL powers and one or more pre-operative measurements of another eye.

12. The prediction engine of claim 11, wherein the subset of IOL implantation records is selected to evaluate a second plurality of prediction model candidates, wherein each of the second plurality of prediction model candidates estimates an IOL power based on a set of pre-operative eye measurements and a desired post-operative MRSE, wherein the prediction engine is further configured to:
evaluate the second plurality of prediction model candidates based on deviations between estimated IOL powers produced by each of the second plurality of prediction model candidates using eye measurement data in the selected subset of historical IOL implantation records and actual IOL powers indicated in the selected subset of historical IOL implantation records;
select a second prediction model from the second plurality of prediction model candidates based on the evaluating; and
calculate a second IOL power using the second prediction model based on the predetermined post-operative MRSE value and the one or more pre-operative measurements of the eye.

13. The prediction engine of claim 11, wherein the prediction engine is further configured to determine the set of available IOL powers from a plurality of IOL powers based on the first IOL power, wherein the set of available IOL powers is within a predetermined threshold from the first IOL power.

14. The prediction engine of claim 11, wherein the subset of historical IOL implantation records is limited to a particular number of records, wherein the prediction engine is further configured to determine the particular number based on an offline analysis of the plurality of historical IOL implantation records.

15. The prediction engine of claim 14, wherein the subset of historical IOL implantation records is selected from the plurality of historical IOL implantation records using a K-Nearest Neighbor (KNN) algorithm, wherein a parameter in the KNN algorithm corresponds to the particular number.

16. A non-transitory machine-readable medium comprising a plurality of machine-readable instructions which when executed by one or more processors are adapted to cause the one or more processors to perform a method comprising:
obtaining one or more pre-operative measurements of an eye for assisting a user to perform an intraocular lens (IOL) implantation in the eye;
selecting, from a plurality of historical IOL implantation records, a subset of historical IOL implantation records for evaluating a first plurality of prediction model candidates based at least on the one or more pre-operative measurements of the eye, wherein each of the first plurality of prediction model candidates estimates a post-operative manifest refraction in spherical equivalent (MRSE) based on a set of pre-operative eye measurements and an IOL power;
evaluating the first plurality of prediction model candidates based on deviations between estimated post-operative MRSEs produced by each of the first plurality of prediction model candidates using eye measurement data in the selected subset of historical IOL implantation records and actual post-operative MRSEs indicated in the selected subset of historical IOL implantation records;
selecting a first prediction model from the first plurality of prediction model candidates based on the evaluating;
calculating, using the selected first prediction model, a plurality of estimated post-operative MRSE values based on a set of available IOL powers and the one or more pre-operative measurements of the eye;
determining, from the set of available IOL powers, a first IOL power corresponding to a first estimated post-operative MRSE value from the plurality of estimated post-operative MRSE values that matches a predetermined post-operative MRSE value;
providing the determined first IOL power to the user to aid in selection of an IOL for implantation in the eye;
obtaining post-operative measurements of the eye including an actual post-operative MRSE value of the eye subsequent to the IOL being implanted in the eye; and
retraining the selected first prediction model based on the actual post-operative MRSE value, wherein subsequent to the retraining, the retrained first prediction model is configured to be utilized for calculating another plurality of estimated post-operative MRSE values based on the set of available IOL powers and one or more pre-operative measurements of another eye.

17. The non-transitory machine-readable medium of claim 16, wherein the subset of IOL implantation records is selected to evaluate a second plurality of prediction model candidates, wherein each of the second plurality of prediction model candidates estimates an IOL power based on a set of pre-operative eye measurements and a desired post-operative MRSE, wherein the method further comprises:
  evaluating the second plurality of prediction model candidates based on deviations between estimated IOL powers produced by each of the second plurality of prediction model candidates using eye measurement data in the selected subset of historical IOL implantation records and actual IOL powers indicated in the selected subset of historical IOL implantation records;
  selecting a second prediction model from the second plurality of prediction model candidates based on the evaluating; and
  calculating a second IOL power using the second prediction model based on the predetermined post-operative MRSE value and the one or more pre-operative measurements of the eye.

18. The non-transitory machine-readable medium of claim 16, further comprising determining the set of available IOL powers from a plurality of IOL powers based on the first IOL power, wherein the set of available IOL powers is within a predetermined threshold from the first IOL power.

19. The non-transitory machine-readable medium of claim 16, wherein the one or more pre-operative measurements of the eye comprise at least one of a corneal power, an axial length, a corneal thickness, an anterior chamber depth, a white-to-white distance, or a manifest refraction in spherical equivalent.

20. The non-transitory machine-readable medium of claim 16, wherein the method further comprises: determining, for the first prediction model, a deviation value based on deviations between estimated post-operative MRSEs produced by the first prediction model using eye measurement data in the selected subset of historical IOL implantation records and actual post-operative MRSEs indicated in the selected subset of historical IOL implantation records; and determining, for each estimated post-operative MRSE value, a predicted MRSE range based on the deviation value, wherein the first IOL power is determined further based on the predicted MRSE range.

* * * * *